United States Patent [19]
Jacobson et al.

[11] Patent Number: 6,036,985
[45] Date of Patent: Mar. 14, 2000

[54] CALCIUM COMPLEX AND FOOD FORTIFIED THEREWITH

[75] Inventors: Mark Randolph Jacobson; Sekhar Reddy, both of New Milford, Conn.; Alexander Sher, Rockville, Md.; Dharam Vir Vaderhra, New Milford; Elaine Regina Wedral, Sherman, both of Conn.

[73] Assignee: Nestec S.A., Vevey, Switzerland

[21] Appl. No.: 09/054,718

[22] Filed: Apr. 3, 1998

[51] Int. Cl.[7] ................. A23L 1/29; A23L 1/304
[52] U.S. Cl. ............... 426/74; 426/575; 426/580; 426/648; 424/439; 424/602
[58] Field of Search ............ 426/74, 575, 648; 424/439, 602

[56] References Cited

U.S. PATENT DOCUMENTS

| | | | |
|---|---|---|---|
| 2,594,439 | 4/1952 | Baker et al. | 426/577 |
| 2,871,123 | 1/1959 | Bauer et al. | 99/54 |
| 4,180,595 | 12/1979 | Lauredan | 426/575 |
| 4,268,533 | 5/1981 | Williams et al. | 426/577 |
| 4,701,329 | 10/1987 | Nelson et al. | 426/74 |
| 4,722,847 | 2/1988 | Heckert | 426/74 |
| 4,834,990 | 5/1989 | Amer | 426/74 |
| 4,840,614 | 6/1989 | Harada et al. | 426/580 |
| 4,851,243 | 7/1989 | Andersen et al. | 426/74 |
| 4,871,554 | 10/1989 | Kalala et al. | 426/74 |
| 4,919,963 | 4/1990 | Heckert | 426/599 |
| 5,389,387 | 2/1995 | Zuniga et al. | 426/74 |
| 5,550,232 | 8/1996 | Keating | 426/74 |
| 5,609,897 | 3/1997 | Chandler et al. | 426/73 |
| 5,851,578 | 12/1998 | Gandhi | 426/74 |
| 5,855,936 | 1/1999 | Reddy et al. | 426/74 |
| 5,928,691 | 7/1999 | Reddy et al. | 426/74 |

FOREIGN PATENT DOCUMENTS

| | | |
|---|---|---|
| 0709033 | 1/1996 | European Pat. Off. . |
| 4111040 | 4/1991 | Germany . |
| 359162847 | 9/1984 | Japan . |
| 436166 | 2/1992 | Japan . |
| 5-238940 | 9/1993 | Japan . |
| 8-56567 | 3/1996 | Japan . |

OTHER PUBLICATIONS

Guamis–Lupez et al., "Calcium enrichment of skimmed milk given UHT Treatment", 1996 Alimentaria, No. 271, pp. 79–82.

*Primary Examiner*—Helen Pratt
*Attorney, Agent, or Firm*—Pennie & Edmonds LLP

[57] ABSTRACT

A metastable calcium complex formed by the interaction of an insoluble calcium source and a solution of citric and lactic acids is described. A fortified foodstuff comprising a fortifying amount of the metastable complex and a process for its preparation by forming the complex then adding the complex to a foodstuff or forming the complex in the foodstuff is disclosed.

16 Claims, No Drawings

CALCIUM COMPLEX AND FOOD FORTIFIED THEREWITH

FIELD OF THE INVENTION

The present invention relates to the fortification of foods and beverages, particularly those containing protein, with calcium.

BACKGROUND OF THE INVENTION

Milk is an important source of dietary calcium. Calcium, the most abundant mineral in body, is a major constituent of bone and teeth. This mineral also plays an important role in several physiological systems. Calcium is important for healthy bone and tooth development in the young and an adequate intake is essential. Calcium status may also be a factor in the development of osteoporosis in elderly people.

Since the body does not produce minerals, it is totally dependent on an external supply of calcium, nutritional or supplementary. The importance of adequate calcium intake is recognized during the whole life of the human being. In 1994, the NIH Consensus Development Panel revised recommended daily allowances for calcium intake for each age group from 800–1200 mg per day to 1500 mg per day.

It has been suggested that calcium in the association with caseins may improve absorption in the gastrointestinal tract. Also it has been found that organic acids salts of calcium are more bioavailable in general than the inorganic salts. Calcium citrate has advantages over other calcium salts for use in fortified foods because of high bioavailability. Calcium citrate, as opposed to calcium in general, has only a marginal effect of interfering with the absorption of other minerals, especially iron. Also, long-term calcium supplementation can reduce with calcium citrate the risk on the formation of kidney and urinary stones since citrate ions are inhibitors for crystallization of stone-forming calcium salts.

Addition of calcium to milk is a very significant problem. Firstly, if we use highly soluble sources of calcium (calcium chloride, etc.) high level of soluble calcium leads to protein coagulation during temperature treatment even at pasteurization temperature. Secondly, slightly soluble sources of calcium will not have destabilization of protein micelles but will precipitate rapidly. Accordingly, the solubility of the calcium sources has to be balanced within a very small range of solubility. Also, very fine forms of colloidal calcium have to be formed in milk in order not to significantly change the ratio between free and bonded calcium. In this case, the order of addition can have significant influence on calcium metastable compounds formation. Another factor which must be considered is the pH of milk with supplements because of it changing during the temperature treatment.

It would be highly desirable to have a calcium source to fortify milk, casein or whey containing beverages and other dairy based products without coagulation and sedimentation, with improved palatability, and without bitterness or off-flavor.

SUMMARY OF THE INVENTION

We have developed a metastable calcium complex with low potassium content formed by the interaction of an alkaline calcium source such as calcium hydroxide, calcium oxide or calcium carbonate with a mixture of lactic and citric acids. The complex can be used to fortify milk, milk beverages, dairy products, nutritional beverages and infant formulas without protein coagulation or salt sedimentation, and with improved palatability due to little or no off-flavors from the presence of potassium ions.

According to the present invention, there is provided a metastable complex formed by the interaction of an alkaline calcium source with a mixture of lactic and citric acids.

DETAILED DESCRIPTION OF THE INVENTION

The alkaline calcium source may be, for instance, calcium hydroxide, calcium oxide or calcium carbonate which is conveniently used in suspension. The mixture of lactic and citric acids is conveniently used as a solution especially an aqueous solution.

Our co-pending U.S. Pat. No. 5,928,691 discloses a metastable calcium citrate-lactate complex formed by mixing solutions of calcium lactate and alkali metal citrate, preferably potassium citrate. The calcium lactate citrate metastable complex represents a form of calcium which is considerably more soluble than calcium citrate, minimizing precipitation of salts in calcium fortified beverages. On the other hand, complex formation has led to decreasing of free ionic calcium content which prevents protein coagulation during the heat treatment of beverages such as milk or other dairy based products. The preferred complex described in this co-pending application is a neutral metastable complex having the formula of $K_3[Ca\ Citr\ Lact_2]$, which has the disadvantage in bitterness due to a high potassium content when the complex is used for fortification in large amount because of potassium to calcium molar ratio (3 moles of potassium per 1 mole of calcium).

In this invention, it is to be understood that "Citr" denotes the formula $^-OOC-CH_2-COH(COO^-)-CH_2-COO^-$, and "Lact" denotes the formula $CH_3-CH(OH)-COO^-$.

Our new calcium lactate-citrate metastable complexes of the present invention are preferably formed by mixing a suspension of the alkaline calcium source, e.g. calcium hydroxide, calcium oxide or calcium carbonate with the desired amount of solution of citric and lactic acids. These complexes possess all the advantages of the previous $K_3[Ca\ Citr\ Lact_2]$ complex but have little or no bitterness due to a reduction/elimination of potassium content. The preferred formula of the metastable complexes with reduced amount of potassium are $K\ [Ca\ Citr_{0.67}Lact]$ and $K_{0.5}\ [Ca\ Citr_{0.67}Lact_{0.5}]$ (calcium to potassium molar ratios are 1:1 and 1:0.5, respectively), and without potassium are $[Ca\ Citr_{0.33}Lact]^0$ and $[Ca\ Citr_{0.5}\ Lact_{0.5}]^0$.

The weight ratio of the citric to lactic acids may be from 0.5:4 to 4:0.5, preferably from 0.75:2.5 to 2.5:0.75 and especially from 1:2 to 2:1.

The weight ratio of the citric and lactic acids to the alkaline calcium source may be from 1.1 to 10:1, preferably from 2:1 to 7.5:1 and especially from 2.5:1 to 5:1.

Advantageously, a carrageenan may be present in the complex which may be the lambda- or iota-form but is preferably kappa-carrageenan. The amount of carrageenan present in the fortified foodstuff may be an amount sufficient to provide from 0.005 to 0.1%, preferably from 0.1 to 0.05%, and more preferably from 0.01 to 0.02% by weight based on the weight of the foodstuff.

According to the present invention, there is also provided a fortified foodstuff comprising a fortifying amount of a complex formed by the interaction of an alkaline calcium source with a mixture of lactic and citric acids.

The fortified foodstuff may be, for instance, an, infant formula, a dairy or soy protein based product, a liquid nutritional product or a confectionery product, e.g. a whole protein product, a hydrolysed whey protein product milk, a casein or a whey containing beverage.

The amount of the complex present in the fortified foodstuff may be from 0.05 to 5%, preferably from 0.1 to 2.5%, and more preferably from 0.2 to 1.3% by weight based on the weight of the foodstuff.

Advantageously, a carrageenan may be added to the foodstuff, preferably before the complex is added to the foodstuff. The carrageenan may be the lambda- or iota-form, but is preferably kappa-carrageenan. The amount of carrageenan present in the fortified foodstuff may be from 0.005 to 0.1%, preferably from 0.1 to 0.05%, and more preferably from 0.01 to 0.02% by weight based on the weight of the foodstuff. The carrageenan may also be added to the foodstuff in the form of an aqueous solution or suspension or as a dry powder.

Instead of forming the complex first and then adding it to the foodstuff, the ingredients of the complex (an alkaline calcium source with a mixture of lactic and citric acids) may be added to the foodstuff to be fortified, e.g. a liquid foodstuff such as milk or a milk beverage, either simultaneously or one after the other where they interact to form the complex. In this embodiment, one or both ingredients may be added in solid form, or as solutions or dispersions to give the fortified foodstuff.

The present invention further provides a process of preparing a fortified foodstuff which comprises adding an alkaline calcium source with a mixture of lactic and citric acids to the foodstuff and forming the complex within the foodstuff.

EXAMPLES

The following examples further illustrate the present invention.

Example 1

The following example demonstrates how to prepare a calcium complex with the formula [Ca $Citr_{0.67}Lact$]$^-$:

Citric acid (2.10 grams) was dissolved in 80 g of water at room temperature. To the solution 2.22 grams of a 50% lactic acid solution was added under agitation. A dispersion of 1.11 grams of calcium hydroxide in 14.57 grams of water at 20° C. was prepared. The calcium hydroxide suspension and the solution of the two acids were combined and mixed for 10 minutes until a clear solution formed. The resulting solution was added to 800 grams of water at 20° C. and the pH is adjusted to 6.6 to 7.0.

The resulting solution was divided into two portions. One portion was stored at room temperature and the other was stored under refrigerated conditions. Samples taken after 2 and 4 weeks were judged to be stable (without sedimentation or coagulation) at both storage conditions. The flavor of the solutions were judged by a taste panel of 3 people to be acceptable by monadic testing.

Example 2

The following example demonstrates how to prepare a calcium complex with the formula [Ca $Citr_{0.67}Lact$]$^-$ and how to use the complex to fortify milk:

Citric acid (2.10 grams) was dissolved in 80 grams of water at room temperature. To the solution, 2.22 grams of a 50% lactic acid solution was added under agitation. A dispersion of 1.11 grams calcium hydroxide in 14.57 grams of water at 20° C. was prepared. The calcium hydroxide suspension and solution of two acids were combined and mixed for 10 minutes until a clear solution was formed.

0.15 grams kappa carrageenan was dissolved in 50 grams of milk. The milk was heated to 165° F. for 5 minutes, then cooled to 20° C. The carrageenan/milk mixture and 4.0 grams of non-fat dry milk were added to 846 grams of milk. The aqueous calcium complex (100 g) was then added to the milk and the pH was adjusted to 6.6 to 7.0.

The fortified milk was pasteurized and stored under refrigerated conditions. The sample was judged to be stable (without sedimentation or coagulation) for 3 weeks. The product flavor was judged by a taste panel of 3 people to be acceptable by monadic testing.

Example 3

The following example demonstrates how to prepare a calcium complex with the formula [Ca $Citr_{0.67}Lact_{0.5}$]$^{0.5-}$:

Citric acid (2.10 grams) was dissolved in 80 grams of water at room temperature. To the solution, 1.11 grams of a 50% lactic acid solution was added under agitation. A dispersion of 1.11 grams calcium hydroxide in 15.68 grams of water at 20° C. was prepared. The calcium hydroxide suspension and solution of two acids were combined and mixed for 10 minutes until a clear solution formed. The resulting solution was added to 800 grams of water at 20° C. and the pH was adjusted to 6.6 to 7.0.

The resulting solution was divided into two portions. One portion was stored at room temperature and the other was stored under refrigerated conditions. Samples taken after 2 and 4 weeks were judged to be stable (without sedimentation or coagulation) at both storage conditions. The flavor of the solutions were judged by a taste panel of 3 people to be acceptable by monadic testing.

Example 4

The following example demonstrates how to prepare a calcium complex with the formula [Ca $Citr_{0.67}Lact_{0.5}$]$^{0.5-}$ and how to use the complex to fortify milk:

Citric acid (2.10 grams) was dissolved in 80 g of water at room temperature. To the solution, 1.11 grams of a 50% lactic acid solution was added under agitation. A dispersion of 1.11 grams calcium hydroxide in 14.57 grams of water at 20° C. was prepared. The calcium hydroxide suspension and solution of two acids were combined and mixed for 10 minutes until a clear solution was formed.

To 50 grams of milk, 0.15 grams kappa carrageenan was dissolved. The milk was heated to 165° F. for 5 minutes, then cooled to 20° C. The carrageenan/milk mixture and 4.0 grams of non-fat dry milk were added to 846 grams of milk. The aqueous calcium complex was then added to the milk and the pH was adjusted to 6.6 to 7.0.

The fortified milk was pasteurized and stored under refrigerated conditions. The sample was judged to be stable (without sedimentation or coagulation) for 3 weeks. The product flavor was judged by a taste panel of 3 people to be acceptable by monadic testing.

Example 5

The following example demonstrates how to prepare a calcium complex with the formula [Ca $Citr_{0.33}Lact$]$^0$:

Citric acid (1.05 grams) was dissolved in 80 grams of water at room temperature. To the solution, 2.22 grams of a 50% lactic acid solution was added under agitation. A dispersion of 1.11 grams calcium hydroxide in 15.62 grams water at 20° C. was prepared. The calcium hydroxide suspension and two acid solutions were combined and mixed for 10 minutes until a clear solution formed. The resulting solution was added to 800 grams of water at room temperature and the pH was adjusted to 6.6 to 7.0.

The resulting solution was divided into two portions. One portion was stored at room temperature and the other was stored under refrigerated conditions. Samples taken after 2 and 4 weeks were judged to be stable (without sedimentation or coagulation) at both storage conditions. The flavor of the solutions were judged by a taste panel of 3 people to be acceptable by monadic testing.

Example 6

The following example demonstrates how to prepare a calcium complex with the formula $[\text{Ca Citr}_{0.33}\text{Lact}]^0$ and how to use the complex to fortify milk:

Citric acid (1.05 grams) was dissolved in 80 grams of water at room temperature. To the solution, 2.22 grams of a 50% lactic acid solution was added under agitation. A dispersion of 1.11 grams calcium hydroxide in 15.62 grams water at 20° C. was prepared. The calcium hydroxide suspension and two acid solutions were combined and mixed for 10 minutes until a clear solution formed.

To 50 grams of milk, 0.15 grams kappa carrageenan was dissolved. The milk was heated to 165° F. for 5 minutes, then cooled to 20° C. The carrageenan/milk mixture and 4.0 grams of non-fat dry milk were added to 868 grams of milk. The aqueous calcium complex was then added to the milk and the pH was adjusted to 6.6 to 7.0.

The fortified milk was pasteurized and stored under refrigerated conditions. The sample was judged to be stable (without sedimentation or coagulation) for 3 weeks. The product flavor was judged by a taste panel of 6 people to be acceptable by monadic testing.

Example 7

The following example demonstrates how to prepare a calcium complex with the formula $[\text{Ca Citr}_{0.5}\text{Lact}_{0.5}]^0$:

Citric acid (1.58 grams) was dissolved in 80 grams of water at room temperature. To the solution, 2.22 grams of a 50% lactic acid solution was added under agitation. A dispersion of 1.11 grams calcium hydroxide in 16.2 grams water at 20° C. was prepared. The calcium hydroxide suspension and two acid solutions were combined and mixed for 10 minutes until a clear solution formed. The resulting solution was added to 800 grams of water at room temperature and the pH was adjusted to 6.6 to 7.0.

The resulting solution was divided into two portions. One portion was stored at room temperature and the other was stored under refrigerated conditions. Samples taken after 2 and 4 weeks were judged to be stable (without sedimentation or coagulation) at both storage conditions. The flavor of the solutions were judged by a taste panel of 6 people to be acceptable by monadic testing.

Example 8

The following example demonstrates how to prepare a calcium complex with the formula $[\text{Ca Citr}_{0.5}\text{Lact}_{0.5}]^0$ and how to use the complex to fortify milk:

Citric acid (1.58 grams) was dissolved in 80 grams of water at room temperature. To the solution, 2.22 grams of a 50% lactic acid solution was added under agitation. A dispersion of 1.11 grams calcium hydroxide in 16.2 grams water at 20° C. was prepared. The calcium hydroxide suspension and two acid solutions were combined and mixed for 10 minutes until a clear solution formed.

To 50 grams of milk, 0.15 grams kappa carrageenan was dissolved. The milk was heated to 165° F. for 5 minutes, then cooled to 20° C. The carrageenan/milk mixture and 4.0 grams of non-fat dry milk were added to 868 grams of milk. The aqueous calcium complex was then added to the milk and the pH was adjusted to 6.6 to 7.0.

The fortified milk was pasteurized and stored under refrigerated conditions. The sample was judged to be stable (without sedimentation or coagulation) for 4 weeks. The product flavor was judged by a taste panel of 6 people to be acceptable by monadic testing.

Example 9

The following example demonstrates how to prepare a calcium complex with the formula $K_{0.5}[\text{Ca Citr}_{0.5}\text{Lact}_{0.5}]^0$:

Citric acid monohydrate (2.10 grams) was dissolved in 60 grams of water at room temperature. To the solution 1.11 grams of a 50% lactic acid solution was added under agitation. A dispersion of 1.11 grams calcium hydroxide in 15.7 grams water at 20° C. was prepared. The calcium hydroxide suspension and two acid solutions were combined and mixed for 10 minutes until a clear solution formed, then solution of 0.42 grams potassium hydroxide in 10 grams of water was added under agitation. The resulting solution was added to 900 grams of water at room temperature and the pH was adjusted to 6.6 to 7.0.

The resulting solution was divided into two portions. One portion was stored at room temperature and the other was stored under refrigerated conditions. Samples taken after 2 and 4 weeks were judged to be stable (without sedimentation or coagulation) at both storage conditions. The flavor of the solutions were judged by a taste panel of 6 people to be acceptable by monadic testing.

Example 10

The following example demonstrates how to prepare a calcium complex with the formula $K_{0.5}[\text{Ca Citr}_{0.5}\text{Lact}_{0.5}]^0$ and how to use the complex to fortify milk: Citric acid monohydrate (2.10 grams) was dissolved in 60 grams of water at room temperature. To the solution 1.11 grams of a 50% lactic acid solution was added under agitation. A dispersion of 1.11 grams calcium hydroxide in 15.7 grams water at 20° C. was prepared. The calcium hydroxide suspension and two acid solutions were combined and mixed for 10 minutes until a clear solution formed, then solution of 0.42 grams potassium hydroxide in 10 grams of water was added under agitation.

In 50 grams of milk, 0.15 grams kappa carrageenan was dissolved. The milk was heated to 165° C. for 5 minutes, then cooled to 20° C. The carrageenan/milk mixture and 4.0 grams of non-fat dry milk were added to 846 grams of milk. The aqueous calcium complex was then added to the milk and the pH was adjusted to 6.6 to 7.0.

The fortified milk was pasteurized and stored under refrigerated conditions. The sample was judged to be stable (without sedimentation or coagulation) for 4 weeks. The product flavor was judged by a taste panel of 6 people to be acceptable by monadic testing.

What is claimed is:

1. A metastable calcium complex having a potassium to calcium ratio of about 1:1 or less and being formed by the interaction of an alkaline calcium source with a mixture of lactic and citric acids.

2. A metastable complex according to claim 1 wherein the alkaline calcium source is calcium hydroxide, calcium oxide, or calcium carbonate.

3. A process of preparing a metastable calcium complex as claimed in claims 1, 3, 4, 5, or 6 comprising mixing a suspension of the alkaline calcium source with the desired amount of a solution of citric and lactic acids for a sufficient time to form the calcium complex.

4. A process according to claim 3 wherein a carrageenan may be present.

5. A process according to claim 4 wherein the carrageenan is kappa-carrageenan.

6. A complex having the formula $K[Ca\ Citr_{0.67}Lact]$.

7. A complex having the formula $K_{0.5}[Ca\ Citr_{0.67}Lact_{0.5}]$.

8. A complex having the formula $[Ca\ Citr_{0.33}Lact]^0$.

9. A complex having the formula $[Ca\ Citr_{0.5}Lact_{0.5}]^0$.

10. A fortified foodstuff that contains a fortifying amount of a calcium complex according to one of claims 1, 6, 7, 8, or 9.

11. A fortified foodstuff according to claim 10 wherein the foodstuff is an infant formula, a dairy or soy protein based product, a liquid nutritional product or a confectionery product.

12. A fortified foodstuff according to claim 10 wherein the amount of the complex present in the fortified foodstuff is from 0.05 to 5% by weight based on the weight of the foodstuff.

13. A process for preparing a fortified foodstuff as claimed in claim 12 which comprises adding an alkaline calcium source with a mixture of lactic and citric acids to the foodstuff and then forming the complex within the foodstuff.

14. A process of preparing a fortified foodstuff as in claim 10 which comprises forming the calcium complex by the interaction of an alkaline calcium source with a mixture of lactic and citric acids and then adding a fortifying amount of the complex to the foodstuff.

15. A process according to claim 14 wherein a carrageenan is present in the fortified foodstuff in an amount of from 0.005 to 0.1% by weight based on the weight of the foodstuff.

16. A fortified foodstuff according to claim 10, wherein the foodstuff comprises a milk.

* * * * *

UNITED STATES PATENT AND TRADEMARK OFFICE
CERTIFICATE OF CORRECTION

Page 1 of 2

PATENT NO.   :   6,036,985

DATED        :   March 14, 2000

INVENTOR(S)  :   Mark JACOBSON et al.

It is certified that error appears in the above-identified patent and that said Letters Patent is hereby corrected as shown below:

Column 6, line 66: claim 3 should be renumbered as claim --7-- so that the claim then correctly depends from claims 1, 3, 4, 5, or 6.

Column 7, line 4: claim 4 should be renumbered as claim --8--; and change the dependency from "claim 3" to --claim 7--.

Column 7, line 6: claim 5 should be renumbered as claim --9--; and change the dependency from "claim 4" to --claim 8--.

Column 7, line 8: claim 6 should be renumbered as claim --3--; and change "$Citr_{067}$" to --$Citr_{0.67}$--.

Column 7, line 9: claim 7 should be renumbered as claim --4--.

Column 7, line 10: claim 8 should be renumbered as claim --5--.

Column 7, line 11: claim 9 should be renumbered as claim --6--.

Column 7, line 12: in claim 10, change the claim dependencies from "claims 1, 6, 7, 8, or 9" to --claims 1, 3, 4, 5, or 6--.

UNITED STATES PATENT AND TRADEMARK OFFICE
CERTIFICATE OF CORRECTION

PATENT NO. : 6,036,985
DATED : March 14, 2000
INVENTOR(S) : Mark Jacobson et al.

It is certified that error appears in the above-indentified patent and that said Letters Patent is hereby corrected as shown below:

Claims 3-10 should now appear as follows:

3. A complex having the formula $K [Ca\ Citr_{0.67}\ Lact]$.

4. A complex having the formula $K_{0.5} [Ca\ Citr_{0.67}\ Lact_{0.5}]$.

5. A complex having the formula $[Ca\ Citr_{0.33}\ Lact]^0$.

6. A complex having the formula $[Ca\ Citr_{0.5}\ Lact_{0.5}]^0$.

7. A process of preparing a metastable calcium complex as claimed in claims 1, 3, 4, 5, or 6 comprising mixing a suspension of the alkaline calcium source with the desired amount of a solution of citric and lactic acids for a sufficient time to form the calcium complex.

8. A process according to claim 7 wherein a carrageenan may be present.

9. A process according to claim 8 wherein the carrageenan is kappa-carrageenan.

10. A fortified foodstuff that contains a fortifying amount of a calcium complex according to one of claims 1, 3, 4, 5, or 6.

Signed and Sealed this

Sixth Day of March, 2001

Attest:

NICHOLAS P. GODICI

Attesting Officer

Acting Director of the United States Patent and Trademark Office